(12) United States Patent
Tanguay et al.

(10) Patent No.: US 7,655,832 B2
(45) Date of Patent: Feb. 2, 2010

(54) RAPID-THROUGHPUT TELEOST REGENERATION ASSAY

(75) Inventors: Robert L. Tanguay, Corvallis, OR (US); Lljoy K. Mathew, Corvallis, OR (US)

(73) Assignee: The State of Oregon Acting by and Through the State Board of Higher Education on Behalf of Oregon State University, Corvallis, OR (US)

( * ) Notice: Subject to any disclaimer, the term of this patent is extended or adjusted under 35 U.S.C. 154(b) by 107 days.

(21) Appl. No.: 11/890,653

(22) Filed: Aug. 6, 2007

(65) Prior Publication Data

US 2008/0057518 A1 Mar. 6, 2008

Related U.S. Application Data

(60) Provisional application No. 60/836,433, filed on Aug. 7, 2006.

(51) Int. Cl.
*G01N 33/00* (2006.01)
*A01K 67/027* (2006.01)
(52) U.S. Cl. ............................................ 800/3; 800/20
(58) Field of Classification Search .................. 800/20, 800/3
See application file for complete search history.

(56) References Cited

U.S. PATENT DOCUMENTS

| | | | |
|---|---|---|---|
| 6,656,449 | B1 | 12/2003 | Serbedzija et al. |
| 7,041,276 | B2 | 5/2006 | Serbedzija et al. |
| 2004/0261143 | A1 | 12/2004 | Mumm et al. |

FOREIGN PATENT DOCUMENTS

WO  WO 2005037070 A2 * 4/2005

OTHER PUBLICATIONS

Langheinrich, U., 2003, BioEssays, 25:904-912.*
Quint et al, 2002, PNAS, 99:8713-8718.*
Geraudie, 1997, Int Jour of Dev Biol, 41:529-532.*
Jeanmarie M. Zodrow et al. 2,3,7,8- Tetrachlorodibenzo-p-dioxin Inhibits Zebrafish Caudal Fin Regeneration, Jul. 18, 2003, Toxicological Sciences 76, pp. 151-161 (2003).
Atsushi Kawakami et al. Early Fin Primordia of Zebrafish Larvae Regenerate by a Similar Growth Control Mechanism with Adult Regeneration, Jun. 28, 2004 Developmental Dynamics 231 pp. 693-699 (2004).
Mathew et al., "Aryl Hydrocarbon Receptor Activation Inhibits Regenerative Growth," *Molecular Pharmacology*, 69(1):257-265, 2006.

* cited by examiner

*Primary Examiner*—Valarie Bertoglio
(74) *Attorney, Agent, or Firm*—Klarquist Sparkman, LLP

(57) ABSTRACT

The present invention provides a method of simultaneously screening at least two candidate agents for an activity affecting regeneration of an embryonic teleost. According to this method, for each agent, a fin of the embryonic teleost is amputated. Next, the amputated teleost is incubated with the candidate agent for a specified period of time. After this period of time, the amputated teleost is imaged. This image is compared to an image of an amputated teleost that was incubated for the specified period of time in the absence of the candidate agent. When comparing the images, a change in morphology of the amputated fin of the embryonic teleost incubated in the presence of the candidate agent compared to the amputated fin of the embryonic teleost raised in the absence of the candidate agent indicates that the candidate agent affects regeneration.

13 Claims, 5 Drawing Sheets

RAPID-THROUGHPUT TELEOST REGENERATION ASSAY

CROSS-REFERENCE TO RELATED APPLICATIONS

This application claims priority from US Provisional Patent Application No. 60/836,433, filed Aug. 7, 2006, which is incorporated herein by reference.

STATEMENT REGARDING FEDERALLY SPONSORED RESEARCH OR DEVELOPMENT

This invention was supported in part by grant number 1R01ES010820 from the National Institute of Health. The U.S. Government has certain rights in the invention

FIELD OF THE INVENTION

The present invention relates generally to regenerative medicine. More particularly, the present invention relates to a rapid-throughput teleost regeneration assay

BACKGROUND

The promise of regenerative medicine is that therapies will be devised to promote the repair or replacement of damaged or diseased tissues and organs. This emerging field is approached from two distinct lines of attack. In recent years, stem cell based models have been developed to generate a suite of differentiated cells for therapeutic applications. The use of high throughput chemical genetic screening to identify modulators of stem cell fate offers great promise. The alternative approach exploits the inherent regenerative capacity of non-mammalian models to define the molecular events that permit tissue regeneration. There are several regenerative animal models including salamanders, newts, hydra and flatworms that have been established to evaluate tissue regeneration; what is currently lacking is the availability of a vertebrate regeneration model that is amenable to rapid throughput assessments. Specifically, in vivo high throughput small molecule screening has the potential to target any biological process; however, this approach has not been applied in a vertebrate regenerative system. Accordingly, there is a need in the art to develop a new system for high throughput screening of small molecules that affect regeneration.

SUMMARY OF THE INVENTION

The present invention provides such a method. Specifically, the present invention provides a method of simultaneously screening at least two candidate agents for an activity affecting regeneration of an embryonic teleost. According to this method, for each candidate agent, a fin of the embryonic teleost is amputated. Next, the amputated teleost is incubated with the candidate agent for a specified period of time. After this period of time, the amputated teleost is imaged. This image is compared to an image of an amputated teleost that was incubated for the specified period of time in the absence of the candidate agent. A change in morphology of the fin of the embryonic teleost in the presence of the candidate agent compared to the fin of the embryonic teleost incubated in the absence of the candidate agent indicates that the candidate agent affects regeneration.

Once a candidate agent has been determined to affect regeneration, it preferably undergoes a secondary screen to aid in identification of the target of the candidate agent. The secondary screen can take many different forms. In one embodiment, the candidate agent is exposed to the amputated teleost for short durations of time at different times after the amputation. In this way, the specific regenerative stage(s) that are sensitive to the candidate agent can be identified. In another embodiment, in situ hybridization, immunohistochemistry, or both are performed on the amputated teleost using regenerative markers. These tests may be performed during, after, or during and after incubation of the teleost with the candidate agent.

In yet another embodiment, the expression of candidate target genes is repressed using antisense morpholine injection.

BRIEF DESCRIPTION OF THE FIGURES

The present invention together with its objectives and advantages will be understood by reading the following description in conjunction with the drawings, in which.

DETAILED DESCRIPTION OF THE INVENTION

Figure 1:
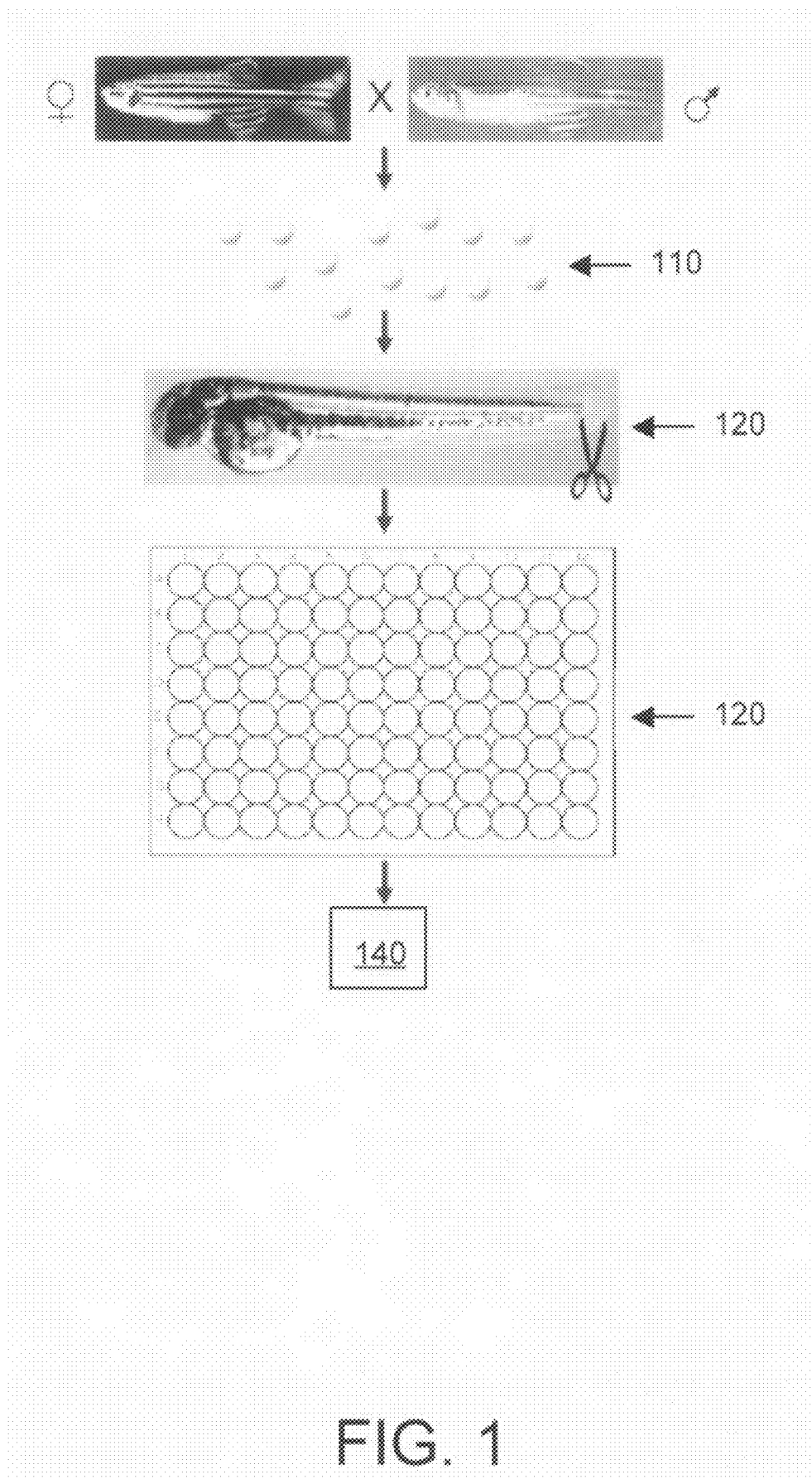
FIG. 1 shows an example of a method of screening candidate agents for an activity affecting regeneration of embryonic teleosts according to the present invention.

The present invention provides a method for simultaneously screening at least two candidate agents for affecting regeneration of an embryonic teleost. The candidate agents may be any type of agent, including but not limited to a peptide, an amino acid, a hormone, a lipid, a small molecule, or a carbohydrate. Preferably, the candidate agents are selected from a library of candidate agents, such as a library of small molecules or chemical compounds. Also preferably, many candidate agents may be screened simultaneously according to the present invention, such that the method is high-throughput.

According to the present method, a first step is to amputate a fin of an embryonic teleost. The teleost may be any teleost but is preferably a zebrafish. Preferably, the teleost is not transgenic. Similarly, any fin may be amputated, but preferably the caudal fin is amputated. The embryonic teleost may be any age at the time of amputation, but is preferably two to three days post fertilization. The fin may be amputated by any means, such as a sterile razor blade or laser cutting tools. Preferably, the fin is amputated using a sterile diamond blade mounted on a micromanipulator. Also preferably, the fin is amputated just posterior to the end of the notochord. Typically, the teleost is anesthetized prior to amputation and the amputation is conducted on a soft surface, such as an agarose-coated Petri dish.

Next, the amputated teleost is incubated with the candidate agent for a specified period of time. Preferably, more than one amputated teleost is incubated with a candidate agent by using multi-well plates. In this way, many candidate agents may be screened simultaneously. Any size multi-well plate may be used, such as a 96-well plate or a 384-well plate. Preferably, the teleosts are incubated in an aqueous buffer containing between about 1 to about 25 µM of the candidate agent. The candidate agent may be present when the amputated teleost is placed in the well, or it may be added immediately afterwards. Also preferably, at least one amputated teleost is incubated in an aqueous buffer without any agent. The amputated teleost may be incubated for any period of time, but is preferably incubated for three days to allow enough time for complete regeneration of the fin to take place. Preferably, the plates are sealed during this time period to prevent evaporation of the buffer and candidate agent using micro titer dish sealing tape or paraffin. Also preferably, the plates are incubated in temperature-controlled chambers. A preferred temperature is 26-28° C.

After the amputated teleost has been incubated for the specified period of time, it is imaged. Preferably, the teleost is not stained prior to this imaging. Also preferably, the imaging is light-microscopic imaging. The images may be captured by, e.g., a CCD camera, for further processing. Alternatively, the images may be acquired directly by the experimenter.

Images of amputated teleosts that were incubated with a candidate agent are then compared with images of amputated teleosts that were incubated in the absence of the candidate agent. This may be accomplished in many ways. For example, the comparison may be done "on-the-fly" by the experimenter by visually inspecting wells containing amputated teleosts incubated with and without candidate agent. In another example, captured images are compared, either visually by the experimenter, or by using a processing device. A change in the morphology of the fin of the embryonic teleost in the presence of the candidate agent as compared to the morphology of the fin of the embryonic teleost in the absence of the candidate agent indicates that the candidate agent affects regeneration. A number of chemical responses are considered positive hits in this assay. For example, the length and area of new tissue distal to the notochord may be measured. A complete positive hit is preferably scored when the area of new tissue is less than 10 percent of that of tissue regeneration in an amputated embryonic teleost incubated in the absence of the candidate agent. Also preferably, if a candidate agent leads to a 10 to 50% reduction in length or area of regeneration compared to an amputated embryonic teleost incubated in the absence of the candidate agent this agent will be considered a putative hit and will be re-screened. A change in the shape of the regenerated tissue in an amputated embryonic teleost incubated in the presence versus the absence of the candidate agent may also be considered a putative positive hit. Finally, the agent impact on overall embryonic development is also preferably defined to determine if an agent is developmentally toxic.

Once candidate agents have been determined to affect regeneration, a number of studies may be done. In one example, the $IC_{50}$ of the candidate agent is determined using methods known in the art. In another example, a secondary screen is performed to aid in identification of a target of the candidate agent. This may be accomplished in many ways. For example, after amputation, the fin undergoes several stages of regeneration. In a first stage, cells migrate into the epithelial wound cap. In a second stage, the blastema differentiates within the wound cap. In a final stage, cells proliferate, leading to outgrowth of the new fin. Thus, by adding the candidate agent to the amputated teleost for short durations of time at different, defined, times after amputation, it is possible to identify which regenerative stage or stages are sensitive to the candidate agent. Specifically, agents present for 0 to 4 hours post amputation (hpa) would preferentially target epithelial wound cap formation. Agents present between 4 and 12 hpa may specifically target blastema formation, and agents present between 12 and 24 hpa may preferentially target cellular differentiation. Finally, agents present between 24 hpa and 72 hpa would target the cellular proliferation stage.

In another embodiment, immunohistochemistry and/or in situ hybridization with regenerative markers is performed on the amputated teleost during, after, or during and after incubation with the candidate agent using methods known in the art. Examples of regenerative markers include, but are not limited to; dlx5, which is used to identify the wound epithelial cap, msxe, which is a well established blastema marker, and junbl which is a more highly expressed blastema marker.

Finally, if the candidate agent is known, the expression of candidate target genes may be repressed using morpholino injection, using techniques known in the art, to target early embryonic gene expression.

EXAMPLES

Methods

Screening for Inhibitors of Larval Fin Regeneration.

Fertilized eggs were obtained from AB strain zebrafish (University of Oregon, Eugene, Oreg.) for all the experiments. All embryos were raised in our laboratory according to standard procedures. Two-day-old embryos were dechorionated and anesthetized with 3-amino benzoic acid ethylester (tricaine). The larvae were laid on an agar plate and the caudal fin primordia were amputated with a surgical blade just posterior to the notochord. Two amputated larvae were arrayed per well in 96 well plates containing 50 μL E3 embryo buffer (5 mM NaCl, 0.17 mM KCl, 0.33 mM CaCl2, 0.33 mM MgSO4). Small molecules (2,000 bioactives from MicroSource Discovery Systems (Gaylordsville, Conn.), were added individually to the test wells at a final concentration of 25 μM. The amputated larvae were incubated for 3 days at 28° C., and at 5 dpa, the larvae were anesthetized and assessed visually to score regenerative progression. After the primary screen, Beclomethasone dipropionate (Beclomethasone, Sigma-Aldrich, St. Louis, Mo.; >99%) was used as a prototype glucocorticoid receptor (GR) agonist. For all functional studies, Beclomethasone was used at 1 μM final concentration.

Adult Zebrafish Study.

Adult male zebrafish (AB strain) were pre-exposed for one day to vehicle or Beclomethasone with waterborne concentrations ranging from 0.05-0.0005 mg/L. After pre-exposure, the fish were anesthetized, and their caudal fins were surgically amputated. The fish were transferred back to the tanks and were continuously exposed to vehicle or Beclomethasone until the end of the study. The exposure solutions were changed daily.

Morpholinos.

Antisense repression of GR was performed using splice variant morpholino (MO) oligonucleotides (Gene Tools, Corvallis, Oreg.). A putative zebrafish GR ortholog was identified (Genbank accession number AB218424). Since there were three predicted transcripts based on alternative splicing, a MO was designed at an intron-exon boundary that was conserved between predicted transcripts. A standard control morpholino (Gene Tools, Corvallis, Oreg.) was used as the control morpholino (Control-MO). Approximately 2 nl of the appropriate MO solution was microinjected into the embryos at the 1-2 cell stage. The 3' end of the MOs was fluorescein tagged to screen microinjection success at 24 hpf. The control and GR morphants at 2 dpf were amputated and exposed to vehicle or Beclomethasone and raised for 3 days at 28° C. The control and PU.1 morphants were amputated and allowed to grow for 3 days at 28° C.

Experimental

Development of Rapid Throughput Zebrafish Regeneration Assay

Figure 2:
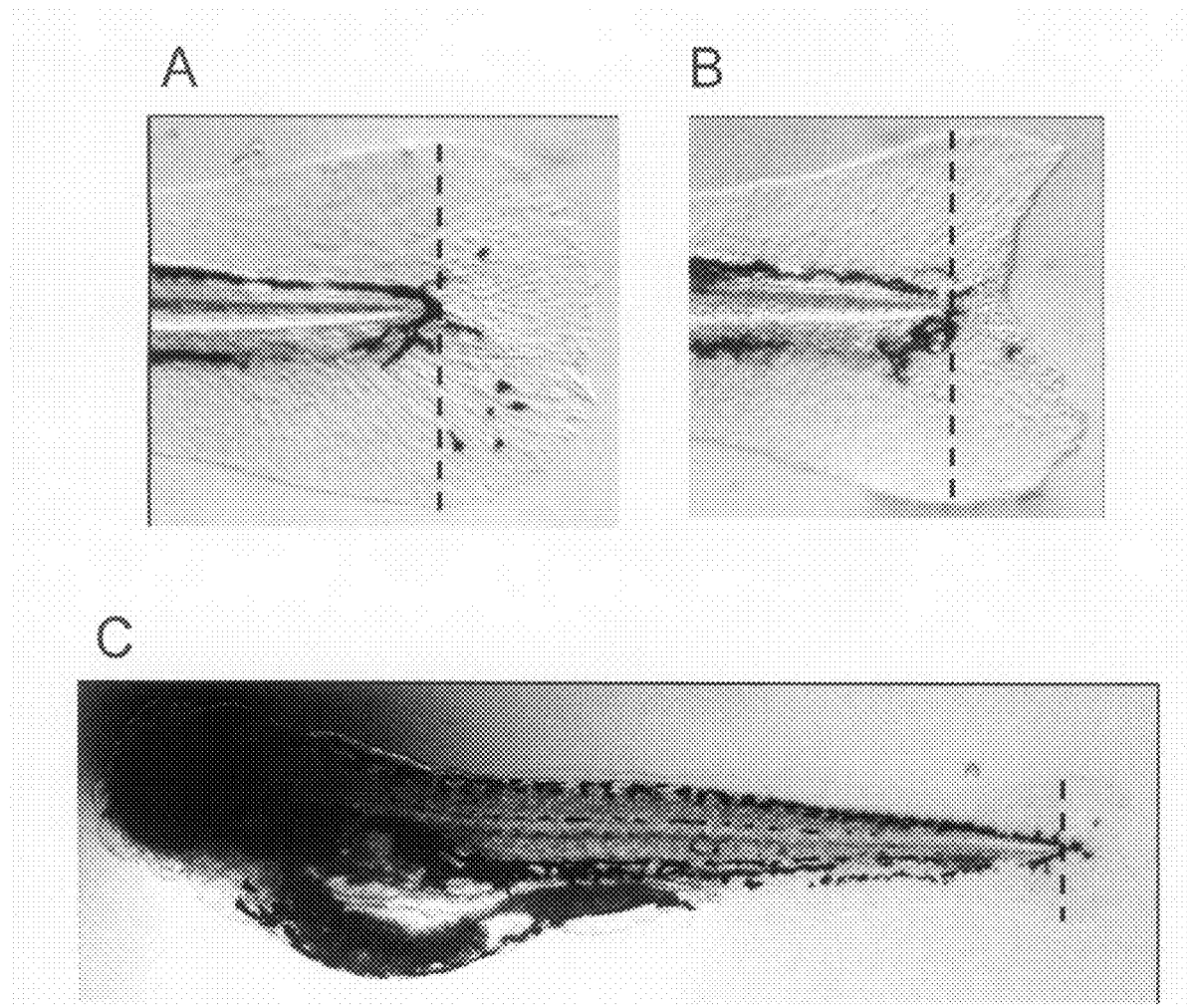
FIG. 2 shows examples of potential outcomes of the method according to the present invention.

Since regeneration is accomplished by an orchestrated co-ordination of multiple pathways and signaling events, a vertebrate regeneration assay was developed to identify small molecules that specifically modulated tissue regeneration (FIG. 1). To demonstrate the power of this approach, a 2000-member structurally diverse bioactive small molecule library was screened to identify inhibitors of regeneration. According to this assay, male zebrafish were mated to female zebrafish to obtain zebrafish fertilized eggs 110. Two days post fertilization (dpf) larvae were amputated 120 and transferred to 96 well plates 130 and continuously exposed to individual chemicals. At 3 day post amputation (dpa), the larvae were microscopically imaged 140 to assess regenerative progression. A total of 17 small molecules (approximately 0.8% of the library) inhibited tissue regeneration. These inhibitory chemicals comprised several different functional classes such as anti-inflammatory, keratolytic, cytochrome P-450 inhibitor etc. Representative images of complete and impaired regeneration are depicted (FIGS. 2A, and B, respectively). Although a number of small molecules produced overt toxicity at the test concentration (25 µM) leading to systemic edema by the end of the assay, these animals completely regenerated their fin tissue (FIG. 2C). In this and subsequent figures, the dashed line indicates the site of amputation. This specificity indicates that a toxic response can be uncoupled from the regenerative response.

Identification of Glucocorticoids as Modulators of Regeneration

Figure 3:
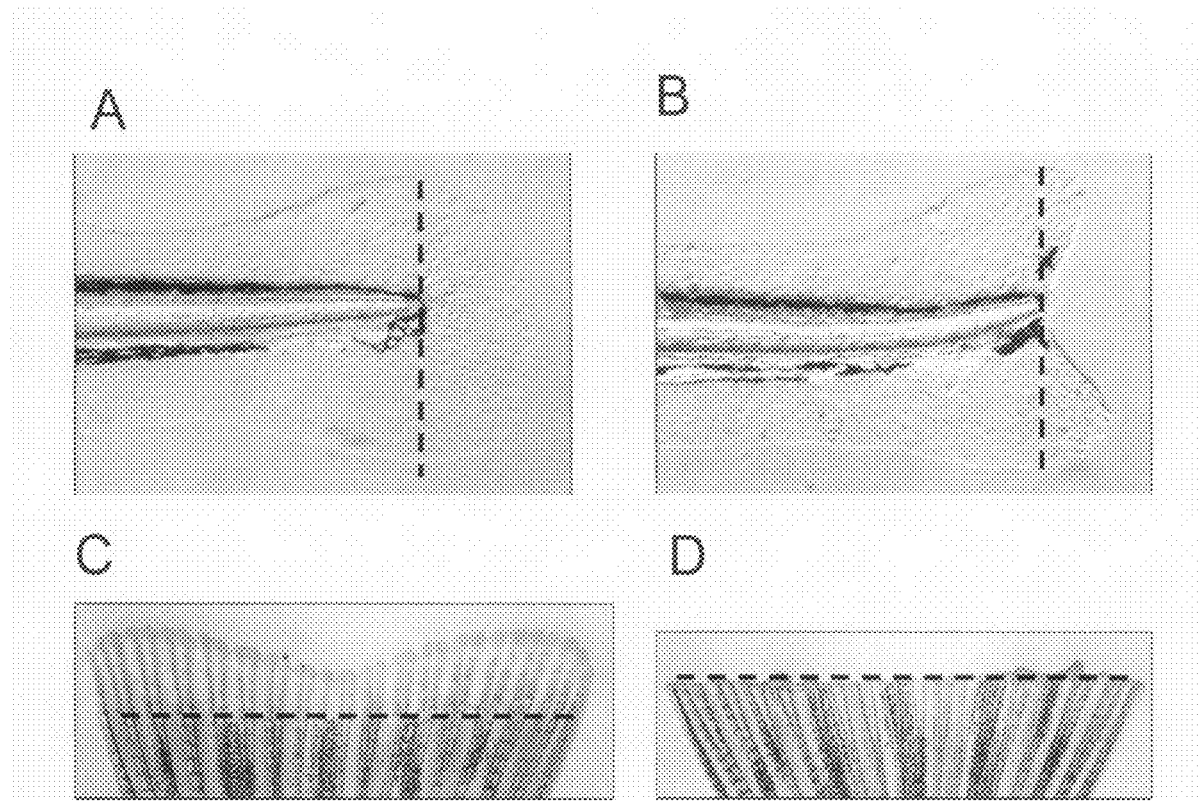
FIG. 3 shows confirmation that a candidate agent identified according to the method of the present invention inhibits adult fin regeneration.

The positive "hits" were of different chemical classes and using structure function analysis, a major cluster of compounds was identified as glucocorticoids (5 of the "hit" compounds). Although the main focus of this study was to demonstrate the feasibility to use small molecule to probe tissue regeneration, we also wanted to demonstrate the ability to rapidly identify small molecule targets during early life stages. We selected glucocorticoids for further studies since this was the largest cluster of "hits". Glucocorticoids specifically inhibited regeneration without inhibiting normal growth, creating a "V" shaped fin (FIG. 3A shows a control regeneration, FIG. 3B shows amputation plus regeneration in the presence of glucocorticoid). This characteristic morphology occurs because the tissue lateral to the amputation plane continues to grow and partially collapses around the amputation plane. Since the adult fin regeneration model is more widely studied, it was important to determine if chemical "hits" identified in the larval screen would be predictive for the adult fin regeneration responses. Therefore, the regeneration response to glucocorticoids exposure on fin regeneration was also assessed in adult zebrafish. Beclomethasone (0.005 mg/L) exposure completely inhibited adult caudal fin regeneration (FIG. 3C shows a control regenerated adult, FIG. 3D, shows an amputated adult incubated with Beclomethasone). As observed in the larvae, Beclomethasone exposure completely abrogated tissue regeneration, as there is essentially no new tissue at 5 dpa. The similar tissue response suggested a common underlying molecular target was targeted by this chemical.

Glucocorticoids are steroid hormones that exert most of their actions by binding the glucocorticoid receptor (GR). From mammalian studies it is clear that there are several isoforms of GR due to differential splicing and alternative translation initiation sites, of which GRα and GRβ are the most well-studied. Binding of glucocorticoid activates GRα transcriptional activity, leading to the initiation or repression of transcription, whereas GRβ is not able to bind ligands and has a dominant negative activity through inhibition of GRα transcriptional activity. In addition to the classical genomic model of GR activation, non-genomic activities have also been reported at high concentrations of glucocorticoids. In order to broadly analyze the mechanism of action from the positive "hits", dose response studies were completed with selected glucocorticoids by measuring the length of maximum outgrowth. The length of maximum outgrowth is the distance between the plane of amputation and the tip of the regenerating fin, and the IC50 for regeneration ranged from 200-400 nM (data not shown).

GR Activation is Required for Beclomethasone to Inhibit Regeneration

Figure 4:
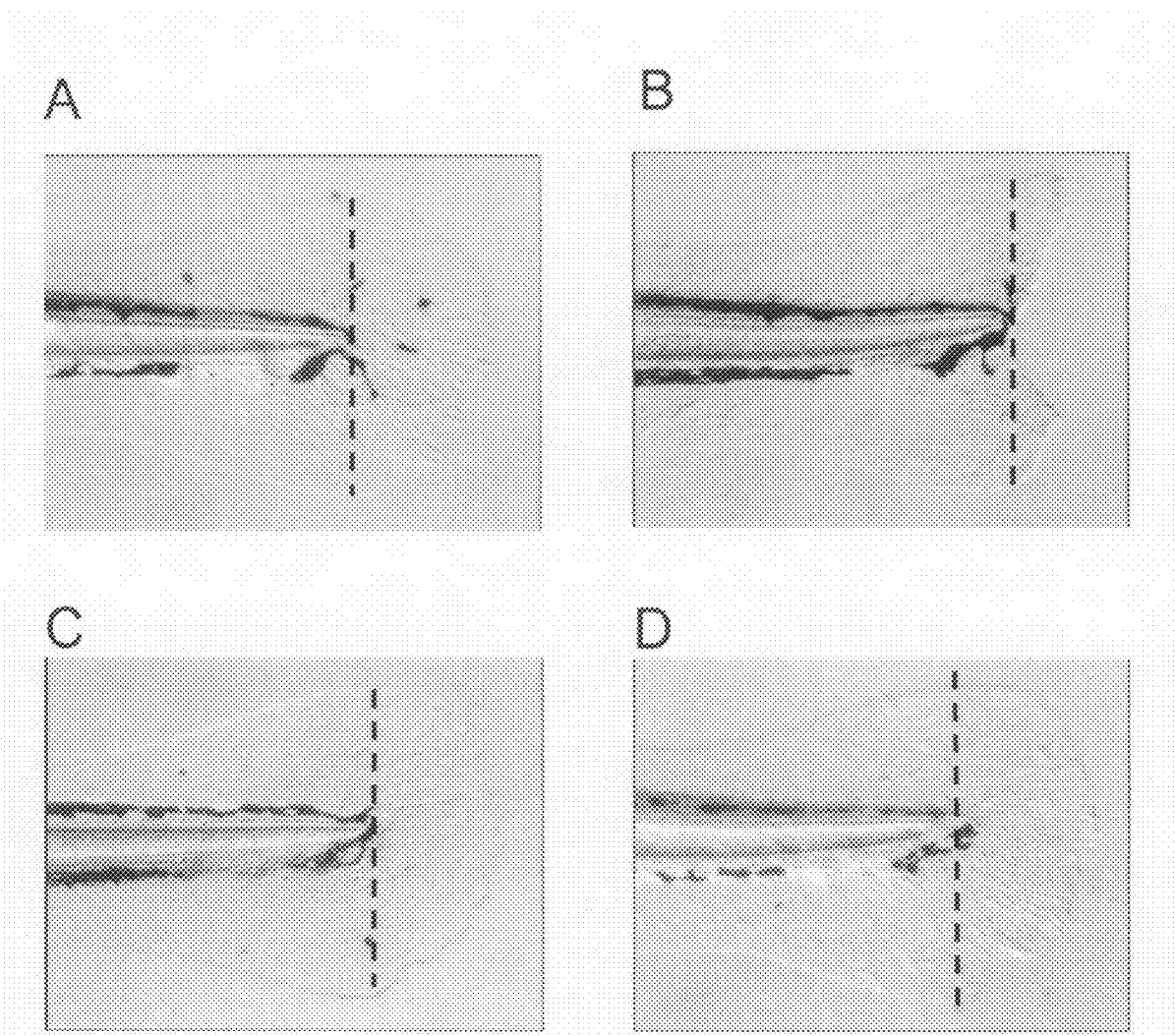
FIGS. 4-5 show examples of secondary screens according to the present invention.

Since the IC50 of glucocorticoids for regeneration was in the nanomolar range, it is highly probable that the glucocorticoids are acting via activation of the GR. To determine whether the GR is activated by one of the "hit" glucocorticoids (Beclomethasone), the expression of three primary GR target genes was analyzed by qRT-PCR in the presence and absence of Beclomethasone (1 µM). All three genes were significantly induced in response to Beclomethasone exposure, indicating that the GR is expressed and can be activated by glucocorticoids at this life stage (data not shown). To directly determine if the GR is necessary for glucocorticoids to inhibit regeneration, a morpholino was designed to block splicing of the exons encoding the well conserved GR ligand binding domain. The standard control morpholino microinjected larvae (morphants) and GR morphants were amputated and exposed to vehicle or Beclomethasone at 2 dpf for 3 days. Control morphants exposed to Beclomethasone failed to regenerate, whereas, knockdown of GR completely restored regenerative capacity, indicating that the inhibition of regeneration was GR dependent. FIG. 4A shows an amputated fin exposed to control morpholino and vehicle, FIG. 4B shows an amputated fin exposed to control morpholino and Beclomethasone, FIG. 4C shows an amputated fin exposed to GR morpholino and vehicle, and FIG. 4D shows an amputated fin exposed to GR morpholino and Beclomethasone. To confirm GR knockdown, qRT-PCR was performed with GR-specific primers in control and GR morphants (data not shown). Altogether, these results indicate that the block in tissue regeneration by Beclomethasone is mediated through ligand activated GR.

Glucocorticoids Target Early Stages of Regeneration

Figure 5:
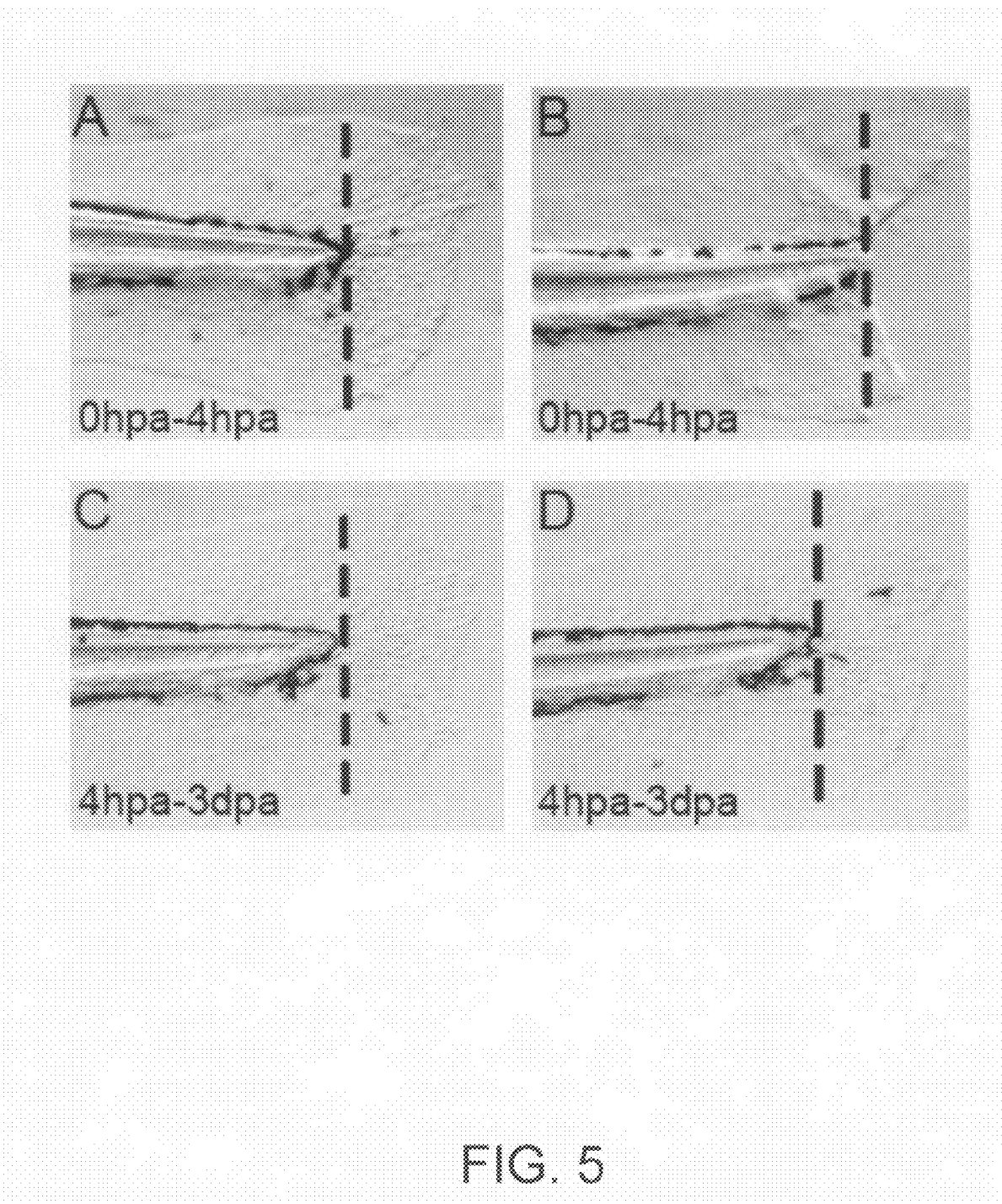

A significant advantage of chemical genetics is that the initiation and termination of the chemical exposure can be tightly controlled; therefore, the screen can be designed to probe any stages of this complex process. To define the regenerative stage that is most responsive to GR activation, Beclomethasone (1 µM) was added beginning at a number of distinct time windows post amputation. Larvae that were exposed to Beclomethasone immediately following amputation for just four hours failed to regenerate (FIG. 5B; 5A shows a control). However, larvae exposed to Beclomethasone beginning at 4 hpa and then continuously until 3 dpa were non-responsive, and they completely regenerated their fins (FIG. 5D; 5C shows a control). These data indicate that glucocorticoids exclusively target early stages of regeneration, which encompass wound healing/blastema stages. Specifically, the irreversible inhibitory effects of glucocorticoids in this early window indicate that the targeted signaling molecules are exclusively important to initiate regeneration.

As one of ordinary skill in the art will appreciate, various changes, substitutions, and alterations could be made or otherwise implemented without departing from the principles of the present invention. Accordingly, the scope of the invention should be determined by the following claims and their legal equivalents.

What is claimed is:

1. A method of simultaneously screening at least two candidate agents for activity affecting regeneration of an embryonic teleost, comprising:
    a) amputating a fin of each of at least two embryonic teleosts to create amputated teleosts;
    b) incubating the amputated teleosts each with one of the at least two candidate agents for a specified period of time;
    c) imaging each of the amputated teleosts after said specified period of time; and
    d) comparing the images of each of the amputated teleosts to an image of an amputated teleost that was incubated for said specified period of time in the absence of the at least two candidate agents,
    wherein a difference in the morphology between the fin of an embryonic teleost that was incubated in the presence of a candidate agent and the morphology of the fin of the embryonic teleost that was incubated in the absence of said candidate agent indicates said candidate agent affects regeneration.

2. The method as set forth in claim 1, wherein said incubating is performed in a multi-well plate, and wherein each amputated teleost is incubated with a candidate agent in a different well.

3. The method as set forth in claim 1, wherein said candidate agents are selected from a small molecule library of candidate agents.

4. The method as set forth in claim 1, wherein said fin is a caudal fin.

5. The method as set forth in claim 1, wherein said amputating occurs two or three days post fertilization.

6. The method as set forth in claim 1, wherein said specified period of time is three days.

7. The method as set forth in claim 1, wherein said telcosts are brafish.

8. The method as set forth in claim 1, wherein said candidate agents are incubated at a concentration range between about 1 and about 25 kM.

9. The method as set forth in claim 1, wherein said imaging is light microscopic imaging.

10. The method as set forth in claim 1, wherein said amputating comprises using a sterile diamond blade mounted on a micromanipulator.

11. The method as set forth in claim 1, further comprising determining the $IC_{50}$ of said candidate agent if said candidate agent is determined to affect regeneration.

12. The method as set forth in claim 1, wherein said teleost are unstained prior to said imaging.

13. The method as set forth in claim 1, wherein said teleost are not transgenic.

* * * * *

UNITED STATES PATENT AND TRADEMARK OFFICE
CERTIFICATE OF CORRECTION

PATENT NO.         : 7,655,832 B2                                                    Page 1 of 1
APPLICATION NO.    : 11/890653
DATED              : February 2, 2010
INVENTOR(S)        : Tanguay and Mathew It is certified that error appears in the above-identified patent and that said Letters Patent is hereby corrected as shown below:

On the Cover:

Under "Inventors," "Lljoy" should read --Lijoy--.

In the Claims:

Column 8, lines 11 and 12, Claim 7, "wherein said telcosts are brafish." should read --wherein said teleost is a zebrafish.--.

Column 8, line 15, Claim 8, "about 25 kM." should read --about 25 µM.--.

Signed and Sealed this

Thirtieth Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,832 B2 | Page 1 of 1 |
| APPLICATION NO. | : 11/890653 | |
| DATED | : February 2, 2010 | |
| INVENTOR(S) | : Tanguay and Mathew | |

It is certified that error appears in the above-identified patent and that said Letters Patent is hereby corrected as shown below:

In the Specification:

*Column 1, lines 11-12*:

"STATEMENT REGARDING FEDERALLY SPONSORED RESEARCH OR DEVELOPMENT should read:

--STATEMENT OF GOVERNMENT SUPPORT--.

*Column 1, line 14*: "was supported in part by grant" should read --was made with government support under grant--.

Signed and Sealed this

Eighteenth Day of October, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,832 B2 | Page 1 of 1 |
| APPLICATION NO. | : 11/890653 | |
| DATED | : February 2, 2010 | |
| INVENTOR(S) | : Tanguay and Mathew | |

It is certified that error appears in the above-identified patent and that said Letters Patent is hereby corrected as shown below:

In the Specification:

*Column 1, lines 11-12*:

"STATEMENT REGARDING FEDERALLY SPONSORED RESEARCH OR DEVELOPMENT"

should read:

--STATEMENT OF GOVERNMENT SUPPORT--.

*Column 1, lines 14-16, should read:*

--This invention was made with government support under grant number 1R01ES010820 awarded by the National Institutes of Health. The government has certain rights in the invention.--.

This certificate supersedes the Certificate of Correction issued October 18, 2011.

Signed and Sealed this
Twenty-seventh Day of March, 2012

David J. Kappos
*Director of the United States Patent and Trademark Office*